(12) United States Patent
Durand et al.

(10) Patent No.: US 9,547,004 B2
(45) Date of Patent: Jan. 17, 2017

(54) RAPID QUANTIFICATION OF BIOMOLECULES IN A SELECTIVELY FUNCTIONALIZED NANOFLUIDIC BIOSENSOR AND METHOD THEREOF

(75) Inventors: Nicolas Durand, Vionnaz (CH); Iwan Märki, Yverdon (CH); Stéphane Broillet, Ferlens (CH); Annick Mayor, Morges (CH); Theo Lasser, Denges (CH)

(73) Assignee: ABIONIC SA, Lausanne (CH)

( * ) Notice: Subject to any disclaimer, the term of this patent is extended or adjusted under 35 U.S.C. 154(b) by 433 days.

(21) Appl. No.: 14/003,277

(22) PCT Filed: Feb. 6, 2012

(86) PCT No.: PCT/IB2012/050527
§ 371 (c)(1),
(2), (4) Date: Nov. 5, 2013

(87) PCT Pub. No.: WO2012/120387
PCT Pub. Date: Sep. 13, 2012

(65) Prior Publication Data
US 2014/0256573 A1   Sep. 11, 2014

(30) Foreign Application Priority Data
Mar. 9, 2011 (WO) .................. PCT/IB2011/050979

(51) Int. Cl.
*C12M 1/34* (2006.01)
*G01N 33/543* (2006.01)
(Continued)

(52) U.S. Cl.
CPC ... *G01N 33/54373* (2013.01); *B01L 3/502746* (2013.01); *B01L 3/502753* (2013.01);
(Continued)

(58) Field of Classification Search
None
See application file for complete search history.

(56) References Cited

U.S. PATENT DOCUMENTS

| 4,775,637 | A | * | 10/1988 | Sutherland | ............ | G01N 21/03 250/227.21 |
| 4,978,503 | A | * | 12/1990 | Shanks | .................. | G01N 21/03 156/61 |

(Continued)

FOREIGN PATENT DOCUMENTS

| JP | 2010-133921 A | 6/2010 |
| WO | WO 2010/042007 | 4/2010 |

(Continued)

OTHER PUBLICATIONS

Lin et al. "One-dimensional dynamics and transport of DNA molecules in a quasi two-dimensional nanoslit", Macromolecules, 2009, 42, 1770-1774.*

(Continued)

*Primary Examiner* — Chris L Chin
(74) *Attorney, Agent, or Firm* — Nixon & Vanderhye P.C.

(57) ABSTRACT

A method and device for the rapid quantification of biomolecules (320) present in a nanochannel (210) is claimed. In particular, the present invention relates to a novel concept of liquid actuation and selectively functionalized surfaces in a nanochannel that create a concentration gradient of transitory immobilized biomolecules (340) across the nanochannel. The present concept enables the quantification of biomolecular interactions of interest (320).

9 Claims, 6 Drawing Sheets

(51) Int. Cl.
  *B01L 3/00* (2006.01)
  *G01N 21/64* (2006.01)
  *B82Y 30/00* (2011.01)
  *B82Y 15/00* (2011.01)
  *B82Y 35/00* (2011.01)
  *G01N 21/03* (2006.01)
  *G01N 21/05* (2006.01)

(52) U.S. Cl.
  CPC .......... *B82Y 30/00* (2013.01); *G01N 21/6428* (2013.01); *G01N 21/6452* (2013.01); *B01L 2300/0819* (2013.01); *B01L 2300/0877* (2013.01); *B01L 2400/0406* (2013.01); *B82Y 15/00* (2013.01); *B82Y 35/00* (2013.01); *G01N 2021/0346* (2013.01); *G01N 2021/058* (2013.01)

(56) References Cited

U.S. PATENT DOCUMENTS

| | | | |
|---|---|---|---|
| 5,637,469 A | * | 6/1997 | Wilding .............. B01J 19/0093 366/DIG. 3 |
| 2010/0144020 A1 | | 6/2010 | Kim et al. |
| 2010/0267158 A1 | | 10/2010 | Chou et al. |
| 2010/0310421 A1 | | 12/2010 | Oliver et al. |
| 2011/0201509 A1 | | 8/2011 | Tegenfeldt et al. |
| 2012/0070846 A1 | | 3/2012 | Kameoka et al. |

FOREIGN PATENT DOCUMENTS

| | | |
|---|---|---|
| WO | 2010/085658 A1 | 7/2010 |
| WO | WO 2011/064701 | 6/2011 |

OTHER PUBLICATIONS

Yang et al. "DNA-functionalized nanochannels for SNP detection", Nano Letters, 2011, 11, 1032-1035.*
International Search Report for PCT/IB2012/050527 mailed May 31, 2012.
Written Opinion of the International Searching Authority mailed May 31, 2012.
Lin et al., "One-Dimensional Dynamics and Transport of DNA Molecules in a Quasi-Two-Dimensional Nanoslit", Macromolecules, American Chemical Society, vol. 42, No. 5, Mar. 10, 2009, pp. 1770-1774.
Jo et al., "A Single-Molecule Barcoding System Using Nanoslits for DNA Analysis", Proceedings of the National Academy of Sciences, National Academy of Sciences, vol. 104, No. 8, Feb. 20, 2007, pp. 2673-2678.
Yang et al., "DNA-Functionalized Nanochannels for SNP Detection", Nano Letters, vol. 11, No. 3, Feb. 16, 2011, pp. 1032-1035.
Notice of Reasons for Rejection mailed Nov. 10, 2015, issued in Japanese Patent Application No. 2013-557188 and English translation.

* cited by examiner

RAPID QUANTIFICATION OF BIOMOLECULES IN A SELECTIVELY FUNCTIONALIZED NANOFLUIDIC BIOSENSOR AND METHOD THEREOF This application is the U.S. national phase of International Application No. PCT/IB2012/050527 filed 6 Feb. 2012 which designated the U.S. and claims priority to PCT/IB2011/050979 filed 9 Mar. 2011, the entire contents of each of which are hereby incorporated by reference.

FIELD OF INVENTION

The present invention relates to methods and devices for the detection of fluorescently labeled biomolecules in selectively functionalized nanofluidic biosensors, using an optical system. The present invention may advantageously be used for rapid quantification of biomedical and biological samples.

BACKGROUND OF THE INVENTION

Nanofluidic biosensors are defined as fluidic systems with nanometer-sized confinements and/or lateral apertures, which are used to quantify the presence of biomolecules in a solution. A majority of the current nanofluidic biosensor developments are intended for bioengineering and biotechnology applications. In the scope of this invention, biosensors are used to quantify the presence of biomolecules in solution for in vitro diagnostic applications.

Swiss patent application CH 01824/09 discloses biosensors with lateral apertures for the detection of biomolecular interactions and PCT application IB2010/050867 discloses their use with simple optical systems. The diffusion of biomolecules in these configurations are slow and require either long waiting times to attain stable measurement conditions or highly concentrated solutions for the observation of the biomolecular interactions.

Biomarkers, also called biological markers, are substances used as specific indicators for detecting the presence of biomolecules. It is a characteristic that is objectively measured and evaluated as an indicator of biological processes, pathogenic processes, or pharmacologic responses to a therapeutic intervention.

Current practices for the detection of specific biomolecules can be divided in two categories: (a) the labeled techniques and (b) the label-free techniques.

Among the labeled techniques, the widely used are fluorescence, colorimetry, radioactivity, phosphorescence, bioluminescence and chemiluminescence. Functionalized magnetic beads can also be considered as labeling techniques. Labeled techniques advantages are the sensitivity in comparison to label-free methods and the molecular recognition due to specific labeling.

Among the label-free techniques, the widely used are electrochemical biosensors, referring to amperometric, capacitive, conductometric or impedimetric sensors, which have the advantage of being rapid and inexpensive. They measure the change in electrical properties of electrode structures as biomolecules become entrapped or immobilized onto or near the electrode, but all these concepts lack molecular specific contrast, sensitivity and reliability.

Enzyme linked immunosorbent assay (ELISA) is an important biochemical technique mainly used to detect the presence of soluble biomolecules in serum, and thus is widely used as diagnostic tool in medicine and quality control check in various industries. ELISA analysis are however expensive, require large amounts of solution and is time consuming.

The other important technologies for biomolecular diagnostics are Western and Northern blots, protein electrophoresis and polymerase chain reaction (PCR). However, these methods require highly concentrated analytes and do not allow high throughput samples testing.

OBJECTIVES

It is an object of this invention to provide inexpensive and rapid nanofluidic biosensors, which do not require complex manipulations.

Still another object of the invention is to geometrically confine the optical measurement volume using nanofluidics, and to selectively functionalize nanochannel surfaces in order to obtain a high sensitivity of the biosensor.

Still another object of the invention is to enhance the sensitivity of the detection by forcing a convective flow across a nanometer-sized confinement (nanochannel) in order to increase the probability for the biomolecules to interact with immobilized biomarkers.

These and other objects of the present invention will become increasingly apparent with reference to the following drawings and preferred embodiments.

SUMMARY OF THE INVENTION

This invention is based on the discovery that forcing biomolecules to enter into a nanometer sized confinement that has selectively functionalized surfaces strongly increase the probability for the biomolecules to interact with immobilized biomarkers. This allows quantifying the presence of fluorescently-labeled biomolecules at ultra-low concentration.

This invention is also based on the discovery that monitoring the photobleaching of the fluophores attached to the biomolecules can be used to differentiate between biomolecules that have interacted with biomarkers and are immobilized in the nanochannel, and those that are simply diffusing through the detection volume.

Furthermore, this invention highlights the possibility to use a driving component to force the convective flow of the solution to analyze through the nanochannel.

In the present text the term "driving component" has to be understood as any element, for instance an absorbing element, which can be used for facilitating the solution flow through the nanochannel.

In the scope of this invention, nanofluidics is used because of its high surface-to-volume ratio, meaning that the surfaces included in the detection volume, maximize the probability of the interactions between biomolecules and immobilized biomarkers on surfaces. It also strongly reduces the background signal of the solution due to the small portion of substrate that is within the detection volume.

The invention therefore relates to a biosensor as defined in the claims.

It also relates to an assembly and a method using said biosensor.

DETAILED DESCRIPTION OF THE INVENTION

As used herein, the term "biomolecules" is intended to be a generic term, which includes for example (but not limited to) proteins such as antibodies or cytokines, peptides, nucleic acids, lipid molecules, polysaccharides and virus.

As used herein, the term "nanochannel" is intended to be a generic term, which means well-defined microfabricated structure with at least one nanometer-sized dimension. The nanometer-sized dimension of the nanochannel is defined to be higher than 2 nm because of the size of the smallest biomolecules to be detected that have to enter into the slit and that are in the same order of magnitude. The present invention is limited to nanochannels with a height lower than one micron, because of the range of the detection volume of the optical system that are typically in the same order of magnitude.

Figure 1A:
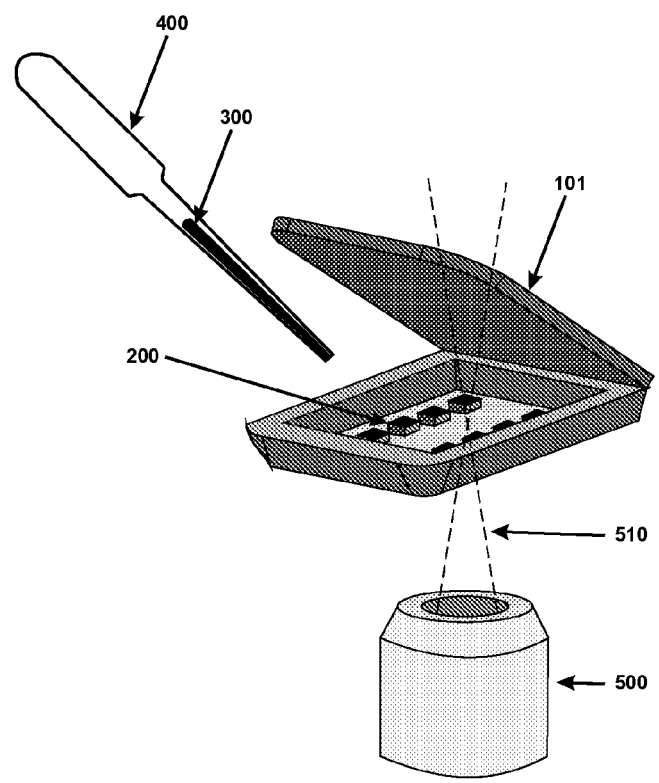
FIG. 1a is a perspective view of a capsule system 101 containing an array of nanofluidic biosensors 200. A solution 300 containing fluorescently-labeled biomolecules is deposited inside the capsule 101 by a pipet system 400. An optical system 500 based on a laser beam 510 is used for the measurement.
Figure 1B:
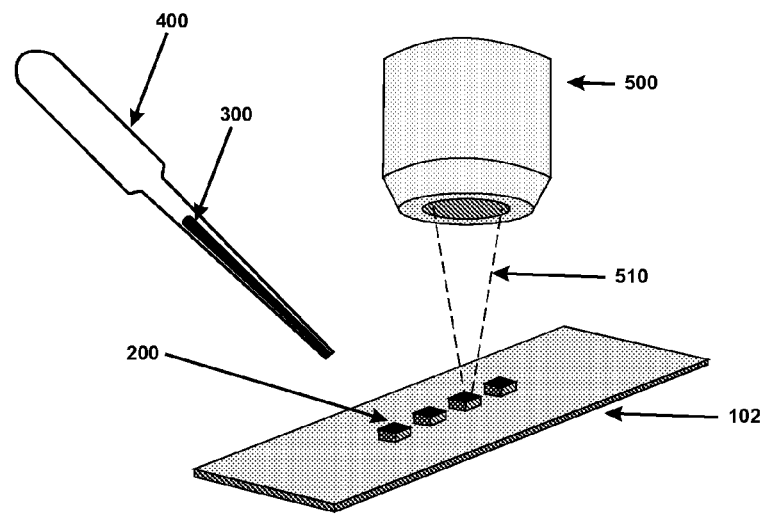
FIG. 1b is a perspective view of a surface 102 containing an array of nanofluidic biosensors 200. A solution 300 containing fluorescently-labeled biomolecules is deposited on the surface 102 by a pipet system 400. An optical system 500 based on a laser beam 510 is used for the measurement.

The present invention aims to enhance the detection of biomolecules by increasing the probability of interactions with specific biomarkers due to the confinement of functionalized surfaces. As shown in FIG. 1a and FIG. 1b, an array of nanofluidic biosensors 200 is immobilized in a capsule system 101 or on a surface 102. A mix solution 300 containing the fluorescently-labeled biomolecules of interest is disposed inside the capsule 101 or on the surface 102 by a pipet system 400. The capsule 101 may be hermetically closed in order to avoid contamination. Finally, an optical unit 500 is used to measure the biomolecular interactions inside the biosensors 200 by focusing the laser beam 510 inside the biosensors nanochannel.

Figure 2A:
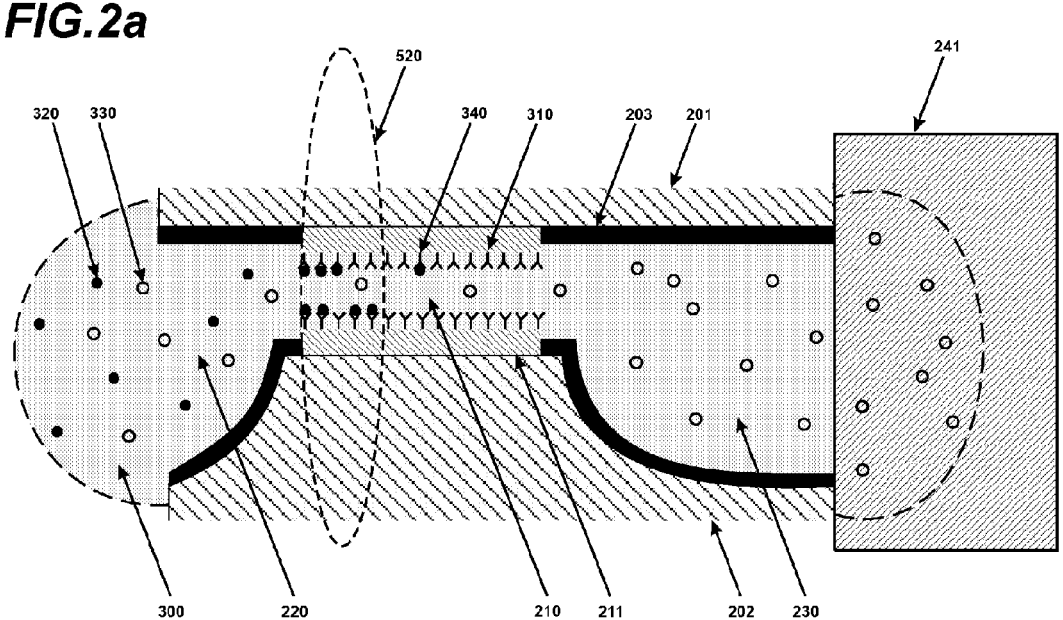
FIG. 2a shows a cross section of the nanofluidic biosensor defined by two substrates 201 and 202 that are locally structured by areas 211 that are functionalized by biomarkers 310 and other areas 203 that prevent that functionalization. Reagent solution 300 containing biomolecules enter the nanochannel 210 and is actuated by the external driving component 241. The laser beam 510 monitors the photobleaching of the immobilized biomolecules 340 in the detection volume 520.
Figure 2B:
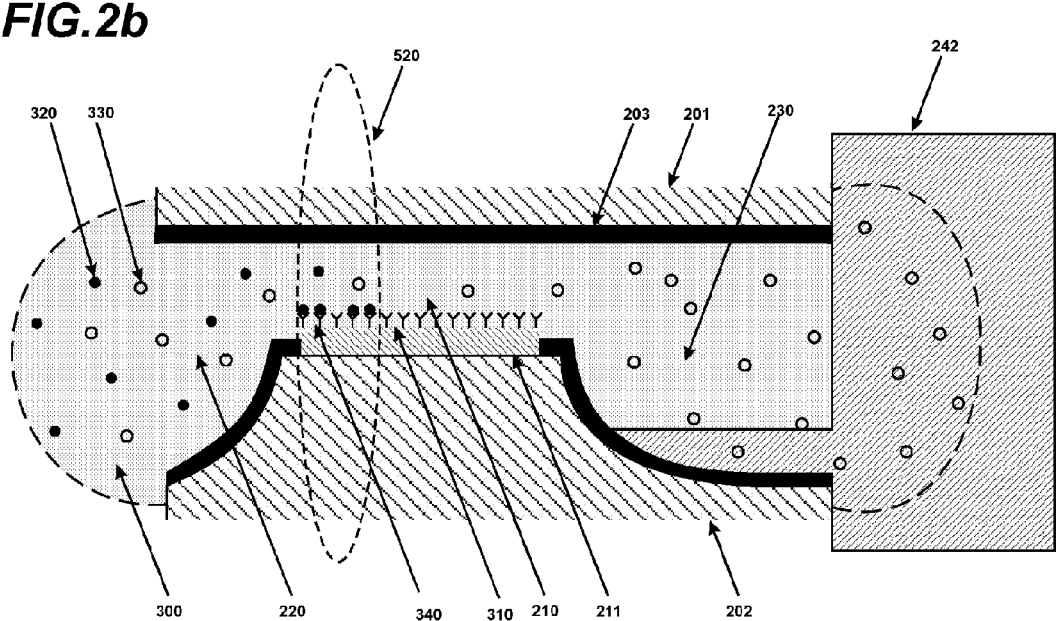
FIG. 2b shows a cross section of the nanofluidic biosensor defined by two substrates 201 and 202. Only one of the substrates is locally structured by area 211 that is functionalized by biomarkers 310 and other areas 203 that prevent that functionalization. Reagent solution 300 containing biomolecules enter the nanochannel 210 and is actuated by the internal driving component 242. The laser beam 510 monitors the photobleaching of the immobilized biomolecules 340 in the detection volume 520.

FIG. 2a and FIG. 2b illustrate the principle of detection and the cross-section of a biosensor according to the invention. The system is composed of a nanochannel 210 linking a lateral input aperture 220 with a lateral output aperture 230. A driving component that can be external (241) or internal (242) is located next to the lateral output aperture 230. First, biomarkers 310 are immobilized on selectively functionalized nanochannel surfaces of one or both substrates 201 and 202. The other nanochannel surfaces and the lateral aperture surfaces may be protected by the deposition of a non-functionalized layer 203. The detection volume 520 has to be focused inside the nanochannel 210 such as the intersection volume defined by the volume of the nanochannel 210 and the detection volume 520 is maximal, and directly next to the lateral input aperture 220. Next, the solution 300 containing the fluorescently labeled specific biomolecules 320 and non-specific biomolecules 330 is filled into the system from the lateral input aperture 220 by capillarity. When reaching the driving component 241 or 242, the solution 300 fills the driving component by absorption for example, leading to a forced convective flow across the biosensor. When the driving component 241 or 242 achieves its maximum filling capacity, the convective flow stops and the system reaches equilibrium. During the convective flow and thanks to Brownian motion, biomolecules 320 interact with the biomarkers 310 immobilized inside the nanochannel 210 and may create molecular complexes 340. A concentration gradient is obtained across the nanochannel 210. The non-specific biomolecules 330 will diffuse in the nanochannel 210 but will not form molecular complexes with the immobilized biomarkers 310. Non-specific biomolecules 331 will be present in the lateral output aperture 230, and some 332 may also be present inside the driving component 241 or 242. When excited by the laser beam 510, the immobilized fluorescently emitting complexes 340 and the diffusing fluorescently emitting biomolecules 330 diffusing across the optical detection volume are both detected by the optical system.

The present invention is distinguishable from techniques currently being used to detect molecular interactions. The unique method of measuring the concentration of immobilized complexes across the selectively functionalized nanochannel being linked to lateral apertures is different from current techniques based on measuring interactions on a single surface or reservoir. These solutions do not benefit from the increased probability of interaction events that occur in the unique design presented in this patent.

Figure 3:
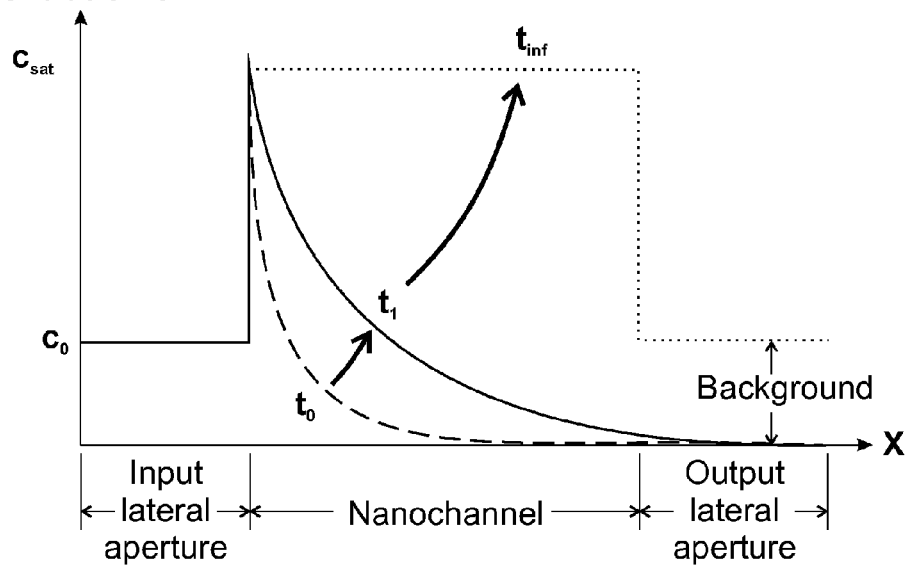
FIG. 3 illustrates the concentration evolution with time of specific biomolecules over the nanochannel length.

FIG. 3 shows the evolution of concentration with time across the biosensor when the solution contains specific biomolecules. Directly after the capillary filling, at time $t_0$, there is a background concentration $c_0$ of fluorescently labeled molecules inside the lateral input aperture. Specific biomolecules that enter into the nanochannel interact quickly with the nanochannel functionalized surfaces, leading to an increase of concentration (dashed curve). The maximum concentration $c_{sat}$ corresponds to the case where, for a given x position, all biomarkers have interacted with specific biomolecules. In function of time, the concentration gradient will tend to the $t_{inf}$ dotted curve, corresponding to the total saturation of the nanochannel biomarkers (dotted curve).

Figure 4:
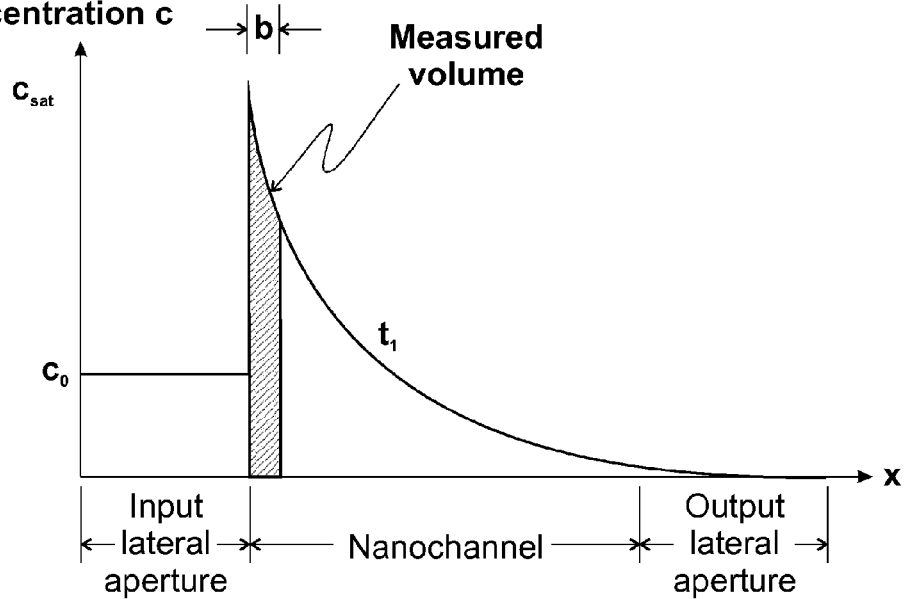
FIG. 4 shows the concentration profile of specific biomolecules over the nanochannel length for a given time $t_1$. The marked area represents the detected portion of specific biomolecules.

FIG. 4 illustrates the concentration gradient across the biosensor at a time $t_1$, corresponding to the case when the solution has already filled the biosensor as well as the absorbing component. Thanks to Brownian motion, the biomolecules continue to enter the nanochannel and continue to interact with the biomarkers, but depending on the background concentration $c_0$, the transition to saturation $t_{inf}$ may be very long. This allows a stable measurement of the concentration profile across the nanochannel. The measurement volume (hatched area) corresponds to the intersection of the laser beam with a width b and the nanochannel.

Figure 5:
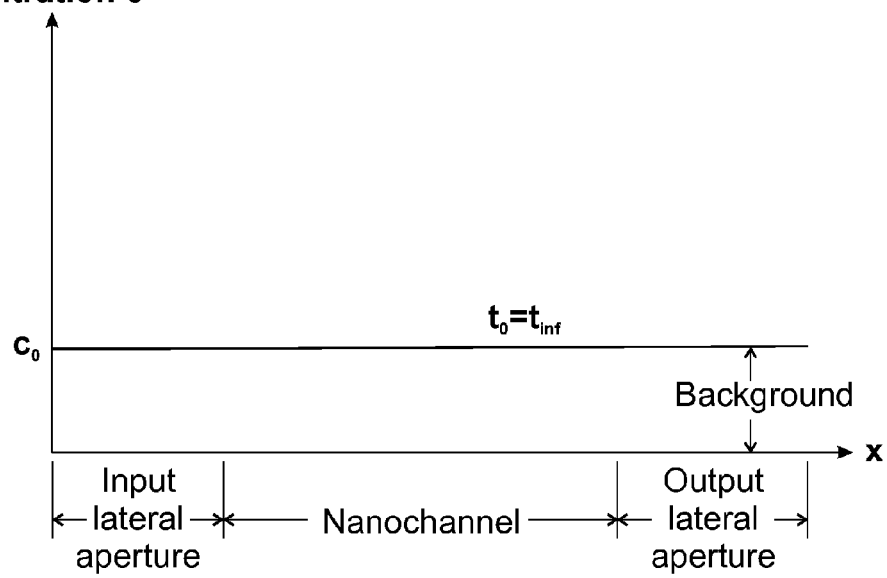
FIG. 5 illustrates the concentration evolution with time of non-specific biomolecules (background) over the nanochannel length.

FIG. 5 shows the concentration evolution with time across the biosensor when the solution contains only non-specific biomolecules. Directly after the capillary filling, at time $t_0$, a background concentration $c_0$ of fluorescently labeled molecules is present inside the lateral input aperture and the nanochannel. No further concentration increase is expected as there is no interaction with the functionalized surfaces. In this case, the concentration $c_0$ remains constant for all x positions and with time.

Figure 6:
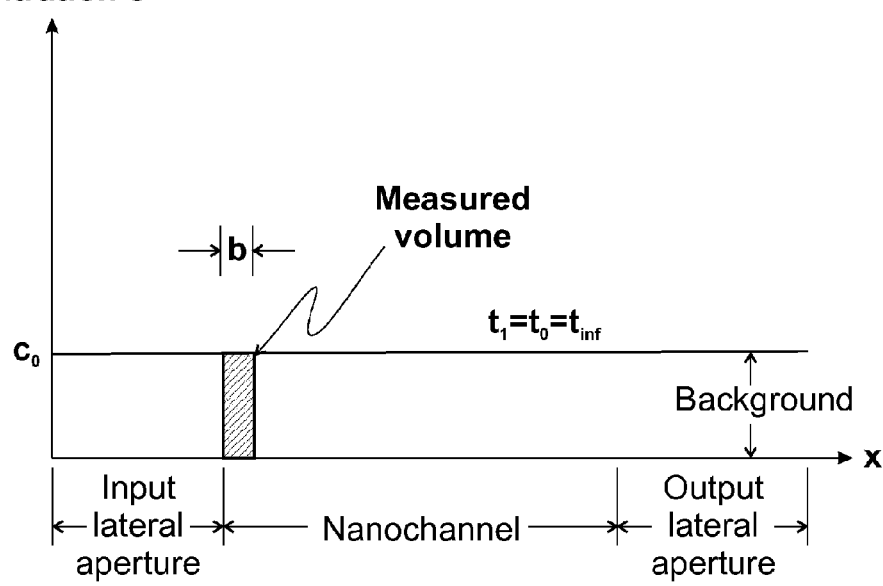
FIG. 6 shows the concentration profile of non-specific biomolecules over the nanochannel length for a given time $t_1$. The marked area represents the detected portion of specific biomolecules, corresponding to the background noise.

FIG. 6 illustrates the concentration gradient across the biosensor at a time $t_1$, corresponding to the case when the solution contains no specific biomolecules and has already filled the biosensor as well as the absorbing component. The measurement volume (hatched area) corresponds to the intersection of the laser beam with a width b and the nanochannel.

Figure 7:
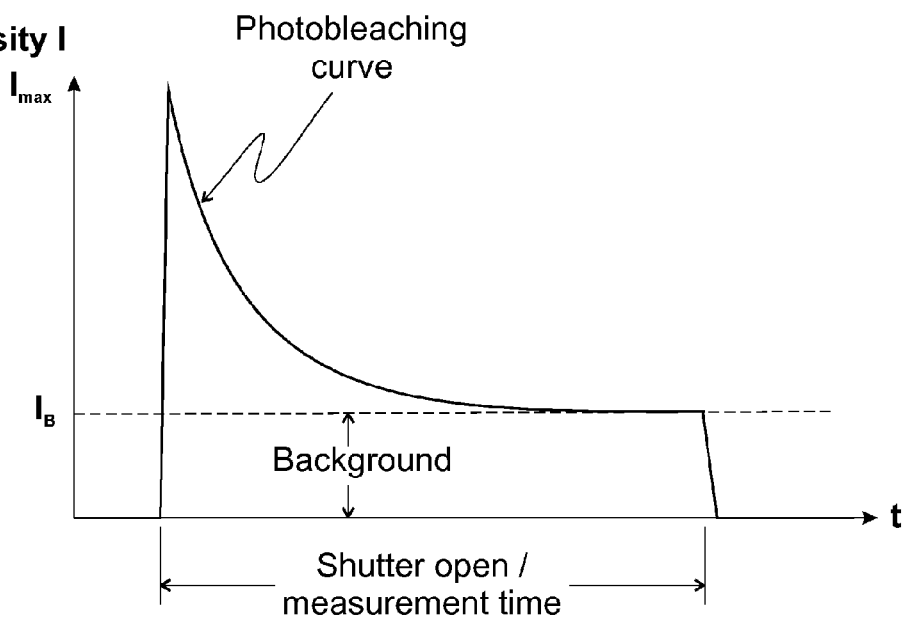
FIG. 7 illustrates a standard photobleaching curve of fluorophores attached to immobilized specific biomolecules.

FIG. 7 shows the fluorescence intensity evolution with time during measurement, for a given position inside the nanochannel, when the solution contains specific biomolecules. The measurement starts when the shutter of the optical system opens. A standard photobleaching curve is obtained containing quantitative information on the number of immobilized and fluorescently-labeled molecules present within the measurement volume.

Figure 8:
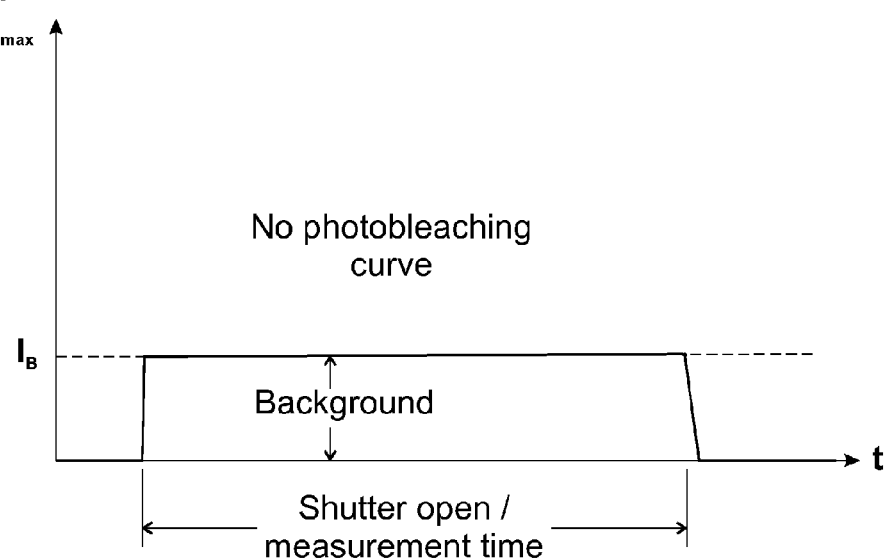
FIG. 8 illustrates the fluorescence intensity curve in function of time for non-specific biomolecules inside the nanochannel, showing that only background noise is detected.

FIG. 8 shows the fluorescence intensity evolution with time during a measurement, for a given position inside the nanochannel, when the solution does not contain any specific biomolecules. The measurement starts when the shutter of the optical system opens. No photobleaching curve is obtained, since there are only diffusing fluorescently-labeled biomolecules inside the measurement volume leading to a constant background signal.

Figure 9:
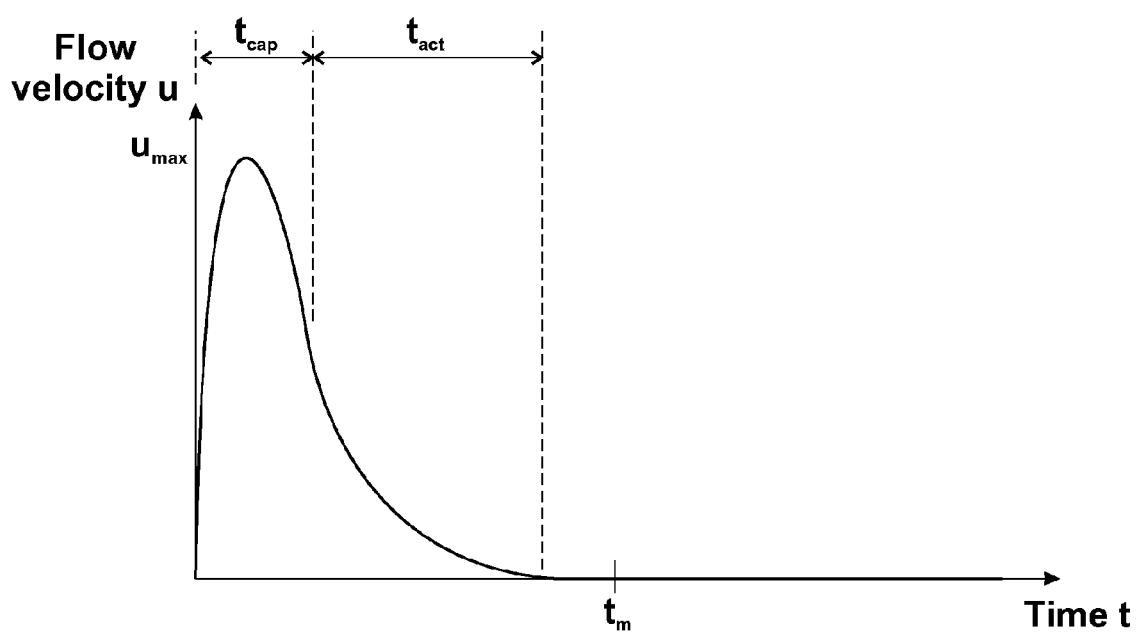
FIG. 9 shows the solution flow velocity inside the nanochannel in function of time.

FIG. 9 shows the evolution of the convective flow of the solution inside the nanochannel in function of time. First, the nanochannel is filled by capillarity during a time $t_{cap}$, which results in an increase of the flow velocity. When reaching the absorbing component, the solution has completely filled the nanochannel and the flow is no more driven by capillarity but rather by absorption. This results in a change of flow velocity during a time $t_{act}$. Finally, the solution flow inside the nanochannel tends to 0, and biomolecule movements are only due to Brownian motion. Measuring time $t_m$ should occur after the convective flow stopped.

According to the present invention, the device offers great improvements for the detection, enumeration, identification and characterization of biomolecules interacting or not with other immobilized biomolecules. Applications of the present invention can cover biomedical, biological or food analysis as well as fundamental studies in analytical and bioanalytical chemistry.

The invention claimed is:

1. A biosensor for detecting and quantifying fluorescently-labeled biomolecules; said biosensor comprising a nanochannel defined between two substrates and containing one or more selectively functionalized areas on which are immobilized biomarkers, said nanochannel further defined by a lateral input aperture and a lateral output aperture, said input aperture is designed to allow a solution containing biomolecules to enter said nanochannel, and said output aperture contains or is in contact with a driving component that drives said solution through said nanochannel by capillarity.

2. Biosensor according to claim 1 wherein said biomarkers biologically or chemically interact with specific biomolecules and/or do not interact with non-specific biomolecules contained in said solution.

3. Biosensor according to claim 1 wherein the substrates are made of a material selected from the group consisting of silicon, glass, plastic and oxide compounds.

4. Biosensor according to claim 1 wherein non-functionalized surfaces inside the nanochannel and the lateral apertures contain a thin layer of material selected from the group consisting of metallic, plastic and oxide compounds, having a thickness between 1 nm and 1000 nm.

5. Biosensor according to claim 1 wherein the lateral apertures have an area from 100 $nm^2$ to 20 $mm^2$ and the nanochannel a height between 2 nm and 1000 nm, a width between 2 nm and 20 mm, and a length between 2 nm and 20 mm.

6. An array comprising several biosensors as defined in claim 1, said biosensors being fixed inside a capsule system or on a surface.

7. An assembly comprising one or more biosensors as defined in claim 1 and comprising optical means for fluorescence excitation and detection.

8. The assembly according to claim 7 wherein said optical means is a fluorescence measurement unit comprising a detector which is a single-photon detector.

9. The assembly according to claim 8 wherein the single-photon detector is a detector array (CMOS or CCD), an avalanche photodiode (APD), or a photomultiplier tube (PMT).

* * * * *